US006204046B1

(12) United States Patent
Chang et al.

(10) Patent No.: US 6,204,046 B1
(45) Date of Patent: Mar. 20, 2001

(54) GORDONA SP. CYKS1 (KCTC 0431BP) CAPABLE OF DESULFURIZING FOSSIL FUEL CONTAINING ORGANIC SULFUR COMPOUNDS

(75) Inventors: Yong Keun Chang; Ho Nam Chang; Sung-Keun Rhee, all of Taejon; Je Hwan Chang; Jung Hyun Sung, both of Seoul, all of (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 09/261,838

(22) Filed: Mar. 3, 1999

(30) Foreign Application Priority Data

Mar. 4, 1998 (KR) .................................................. 98-7159

(51) Int. Cl.⁷ .............................. C12N 1/20; C10G 32/00
(52) U.S. Cl. ........................ 435/252.1; 435/281; 435/282
(58) Field of Search .................................... 435/282, 281, 435/252.1

(56) References Cited

U.S. PATENT DOCUMENTS

| | | |
|---|---|---|
| 5,002,888 | 3/1991 | Kilbane . |
| 5,104,801 | 4/1992 | Kilbane . |
| 5,132,219 | 7/1992 | Kilbane . |
| 5,198,341 | 3/1993 | Kilbane . |

OTHER PUBLICATIONS

Finnerty W.R. Fuel. 1993. vol. 72, No. 12, pp. 1631–1634.*
Finnerty et al. Biotechnol. Bioeng. Symp. 1986, No. 16, pp. 205–221.*
Chun et al. International Journal of Systematic Bacteriology. Jan. 1997, vol. 47, No. 1, pp. 127–131.*
Sung–Keun Rhee et al., Desulfurization of Dibenzothiophene and Diesel Oils . . ., Appl.Environ.Microbiol., 64(6):2327–2331 (1998).
Toshio Omori et al., Desulfurization of Dibenzothiophene by Corynebacterium sp. Strain SY1, Appln.Environ.Microbiol., 58(3):911–915 (1992).
Yoshikazu Izumi et al., Selective Desulfurization of Dibenzothiophene by Rhodococcus erythropolis D–1, Appln.Environ.Microbiol., 60:223–226 (1994).

* cited by examiner

*Primary Examiner*—Irene Marx
*Assistant Examiner*—Vera Afremova
(74) *Attorney, Agent, or Firm*—Darby & Darby

(57) ABSTRACT

The present invention relates to Gordona sp. CYKS1 (KCTC 0431BP) capable of selective removal of organically bound sulfurs from carbonaceous fossil fuel such as petroleum and coal by cleaving bonds between carbon and sulfur atoms in the said sulfur-containing organic compounds, and a method for biological desulfurization using this strain at the room temperature and atmospheric pressure. Since Gordona sp. CYKS1 (KCTC 0431BP) utilizes various organic sulfur compounds in fossil fuel besides dibenzothiophene as a sole sulfur source, the method for biological desulfurization employing the Gordona strain has advantages over the conventional chemical methods as followings: The desulfurization can be carried out at a mild condition; the cost for installation and operation of equipments can be reduced; and, the desulfurization of highly complex organic sulfur compounds can be realized.

1 Claim, 5 Drawing Sheets

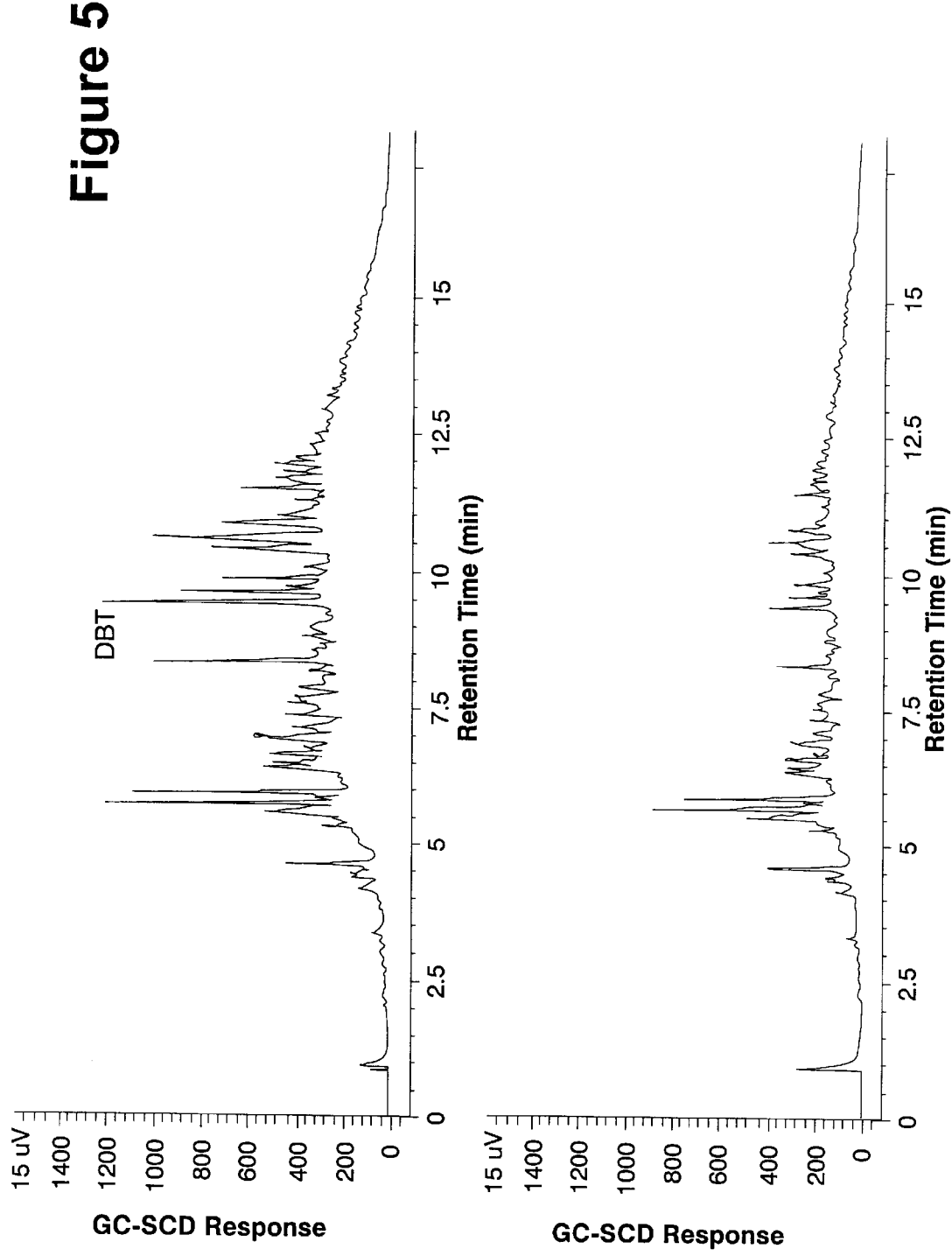

GORDONA SP. CYKS1 (KCTC 0431BP) CAPABLE OF DESULFURIZING FOSSIL FUEL CONTAINING ORGANIC SULFUR COMPOUNDS

FIELD OF THE INVENTION

The present invention relates to Gordona sp. CYKS1 capable of desulfurizing fossil fuel containing organic sulfur compounds, more specifically, to Gordona sp. CYKS1 capable of selective removal of organically bound sulfurs from carbonaceous fossil fuel such as petroleum and coal by cleaving bonds between carbon and sulfur atoms in the said sulfur-containing organic compounds, and a method for biological desulfurization using this strain at the room temperature and atmospheric pressure.

BACKGROUND OF THE INVENTION

Sulfur oxide ($SO_x$), which is generated from the combustion of more than 200 kinds of organic sulfur compounds contained in petroleum, causes not only air pollution but also acid rain and exerts a bad influence on the ecosystem. In this connection, the desulfurization is essential in order to reduce the sulfur contents in fossil fuel. For the desulfurization of petroleum products, the hydrodesulfurization has been conventionally carried out by adding hydrogen at the high temperature of 300–360° C. and high pressure of 35–170 atm.

However, in case of the more complex compounds than dibenzothiophene ("DBT"), which constitutes more than 30% of whole sulfur-containing organic materials in fossil fuel, the hydrodesulfurization is no more effective, and deep desulfurization has been regarded as an alternative way of removing sulfur from these materials, though it depends on the nature of crude oil and its composition.

Under the circumstances, there are strong reasons for exploring and developing a novel desulfurization method which consumes little energy, since the chemical methods such as the hydrodesulfurization and deep desulfurization have been proven less satisfactory in terms of the economy of maintenance, exhaustion of low sulfur-containing crude oil and environmental destruction.

Unlike the prior art chemical methods, biological desulfurization can be carried out at the room temperature and atmospheric pressure. In this regard, desulfurizing bacteria has been utilized for saving the cost for the installation and operation, when compared with previous chemical desulfurization using hydrogen. Especially, the biological method has a merit in a sense that the organic sulfur compounds which are more complex than DBT can be readily desulfurized.

In general, biological desulfurization of fossil fuel using microorganisms may be carried out under the aerobic or anaerobic condition. Accordingly, the desulfurization using aerobic bacteria has advantages as followings: It can be operated in an efficient and speedy manner; it does not consume expensive hydrogen; and, it does not require additives or equipments to maintain the electrical reducing potential and the anaerobic state.

SUMMARY OF THE INVENTION

The present inventors have made an effort to screen desulfurizing bacteria capable of selective removal of organically bound sulfur from carbonaceous fossil fuel from waste water environment contaminated by crude oil, and finally isolated and identified a novel Gordona species which can desulfurize DBT and more comlex organic sulfur compounds at the room temperature and atmospheric pressure.

The primary object of the present invention is, therefore, to provide a novel Gordona species capable of desulfurizing fossil fuel containing organic sulfur compounds.

The other object of the invention is to provide a method for biological desulfurization using the said microorganism.

BRIEF DESCRIPTION OF DRAWINGS

The above and the other objects and features of the present invention will become apparent from the following descriptions given in conjunction with accompanying drawings, in which:

FIG. 5 is a GC-SCD chromatogram of desulfurized diesel oil treated with the whole cell enzyme of Gordona sp. CYKS1.

DETAILED DESCRIPTION OF THE INVENTION

Figure 1:
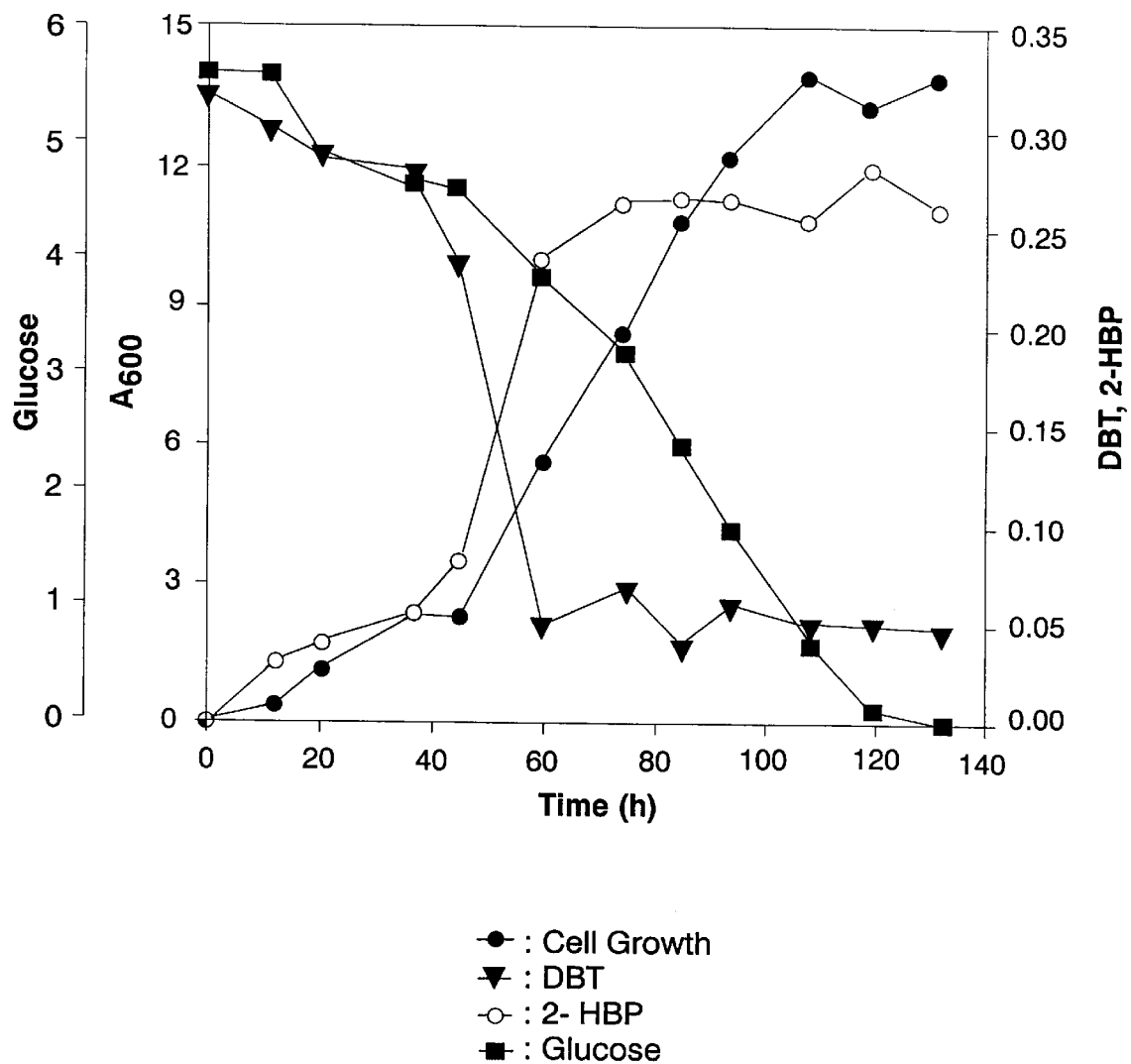
FIG. 1 is a graph showing the elimination of dibenzothiophene by Gordona sp. CYKS1 in dibenzothiophene/ethanol system.

The present inventors have screened a novel desulfurizing bacterium which belongs to Gordona species as followings: Desulfurizing microorganisms are first selected from contaminated waste water by continuous and enrichment culture supplemented DBT, and then cultivated in a growth medium containing DBT as a sole sulfur source. Then, they finally isolated a Gordona sp. strain capable of desulfurizing DBT, which also utilizes various organic sulfur compounds in fossil fuel besides DBT. The Gordona sp. strain thus isolated was designated as 'Gordona sp. CYKS1' and deposited with Korean Collection for Type Cultures (KCTC, #52, Oundong, Yusong-ku, Taejon 305–333, Republic of Korea), an international depository authority as accession No. KCTC 0431BP on Jan. 23, 1998.

As described in Examples below, Gordona sp. CYKS1 (KCTC 0431BP) removes sulfur selectively from DBT and converts DBT to 2-hydroxy biphenyl ("2-HBP") via dibenzothiophene sulfone. The said strain eliminates only sulfur from organic sulfur compounds by the metabolic pathway, without affecting on the other atoms or bond, between carbons in the compounds.

On the other hand, the biological desulfurization of organic sulfur using Gordona sp. CYKS1 strain is performed by inoculating Gordona sp. CYKS1 (KCTC 0431BP) to a minimal salt medium containing organic sulfur compounds and culturing the microorganism under an aerobic condition at the temperature of 20–37° C.

In carrying out the biological desulfurization, the minimal salt medium includes $Na_2HPO_4$ 1.5 g/l, $KH_2PO_4$ 4.5 g/l, $MgCl_2$ 0.2 g/l, $NH_4Cl$ 2 g/l, $CaCl_2$ 0.02 g/l, trace element solution (containing $FeCl_2$ 2100 mg/l, $CoCl_2$ 250 mg/l, $NiCl_2$ 24 mg/l, $MnCl_2$ 100 mg/l, $CuCl_2$ 5 mg/l, $ZnCl_2$ 144 mg/l, boric acid 30 mg/l and $MoCl_3$ 36 mg/l) and vitamin solution (containing folic acid 0.025 mg/l, riboflavin 2 mg/l, lipoic acid 0.05 mg/l, biotin 1 mg/l, nicotinic acid 3.5 mg/l, thiamin chloride 3 mg/l, p-aminobenzoic acid 2 mg/l, pyridoxal chloride 1 mg/l, calcium pantothenate 1 mg/l and vitamin $B_{12}$ 0.5 mg/l).

Organic sulfur compounds which can be desulfurized by the biological desulfurizing method includes methyl sulfide, thiophene, thiazole, 2-methyl thiophene, 3-methyl thiophene, 4,5-dimethyl thiophene, thianaphthene, phenyl sulfide, benzyl sulfide, dibenzothiosulfone, and fossil fuel like crude oil, petroleum and diesel oil containing these organic sulfur compounds.

In desulfurization of materials containing organic sulfur compounds, one or more of the whole cell or the cell extract of Gordona sp. CYKS1 strain, recombinant microorganism harboring genes related to desulfurization and enzyme isolated from these organisms may be utilized.

The present invention is further illustrated in the following examples, which should not be taken to limit the scope of the invention.

EXAMPLE 1

Screening and Identification of Desulfurizing Bacterium

Microorganisms collected from waste water released from the dye industry complex in Taegu, Korea, were employed to investigate their desulfurizing activity by the screening method described in Example 2 below. In this screening, a strain with the highest activity was finally selected and identified (see: Table 1).

Based on the chemotaxonomic analysis of the strain shown in Table 1 and the previous reports in the publication (see. International Journal of Systematic Bacteriology, 47:127–131 (1997)), the selected bacterium is identified as a novel strain belonging to Gordona sp. The strain thus isolated was designated as 'Gordona sp. CYKS1' and deposited with Korean Collection for Type Cultures (KCTC, #52, Oun-dong, Yusong-ku, Taejon 305–333, Republic of Korea), an international depository authority as accession No. KCTC 0431BP on Jan. 23, 1998.

TABLE 1

Chemotaxonomic analysis of Gordona sp. CYKS1

| Analysis | Result |
| --- | --- |
| Quinone | Detected: Menaquinone MK-9($H_2$) |
| Diaminopimelic acid | Detected: meso-diaminopimelic acid |
| Mycolic acid | Detected |

EXAMPLE 2

Desulfurizing Activity of Gordona sp. CYKS1 in Dibenzothiophene/ethanol System

Desulfurizing activity was measured under a growth condition employing a medium containing DBT dissolved in ethanol supplemented as a sole sulfur source. That is, DBT dissolved in anhydrous ethanol was added to the concentration of 0. 3 mM into 20 ml of sterilized minimal salt medium ($Na_2HPO_{4\ 1.5}$ g/l, $KH_2PO_4$ 4.5 g/l, $MgCl_2$ 0.2 g/l, $NH_4Cl$ 2 g/l, $CaCl_2$ 0.02 g/l, trace element solution 1 ml/l and vitamin solution 1 ml/l) containing 10 g/l of glucose. The composition of trace element solution used above was $FeCl_2$ 2100 mg/l, $CoCl_2$ 250 mg/l, $NiCl_2$ 24 mg/l, $MnCl_2$ 100 mg/l, $CuCl_2$ 5 mg/l, $ZnCl_2$ 144 mg/l, boric acid 30 mg/l and $MoCl_3$ 36 mg/l, and vitamin solution includes folic acid 0.025 mg/l, riboflavin 2 mg/l, lipoic acid 0.05 mg/l, biotin 1 mg/l, nicotinic acid 3.5 mg/l, thiamin chloride 3 mg/l, p-aminobenzoic acid 2 mg/l, pyridoxal chloride 1 mg/l, calcium pantothenate 1 mg/l and vitamin $B_{12}$ 0.5 mg/l.

Gordona sp. CYKS1 was inoculated into the medium described above and its growth rate was measured at the appropriate time intervals. After 60 hours of incubation, the concentration of DBT was reduced drastically from 0.3 mM to 0.05 mM, which indicates the elimination of 0.25 mM of DBT from the medium. As shown in FIG. 1, it was demonstrated that 2-HBP was formed as a final product whose increment of is directly proportional to the DBT consumption.

For this analysis, 10 µl of supernatant after ethyl acetate extraction of cell culture broth was injected and fractionated through C18 or phenyl column. Quantitative analysis of DBT and 2-HBP was carried by L-6200 intelligent pump and HPLC (Hitachi, Japan) equipped with L-4200H UV-VIS detector at 280 nm wavelength. Cell mass was determined by measuring the absorbince of culture broth samples at 600 nm ($A_{600}$), the absorbance reached to a value of 14, which corresponds to about 3.1 g (dry weight)/l.

EXAMPLE 3

Figure 2:
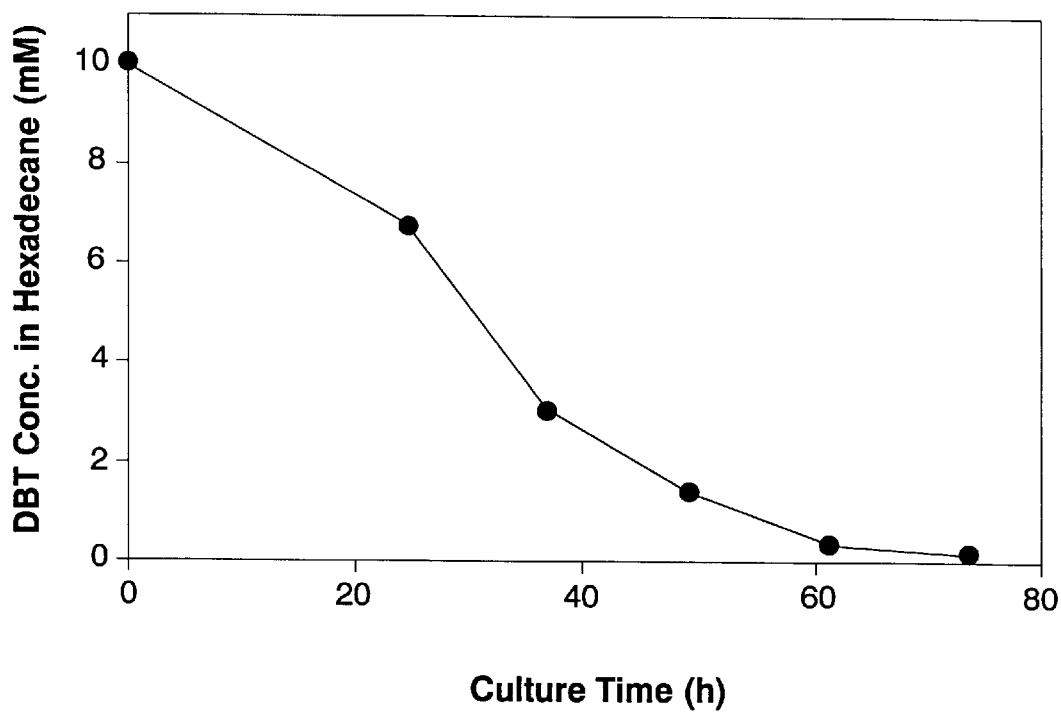
FIG. 2 is a graph showing the elimination of dibenzothiophene by Gordona sp. CYKS1 in dibenzothiophene/hexadecane system.

Desulfurizing Activity of Gordona sp. CYKS1 in Dibenzothiophene/hexadecane System Desulfurizing activity of Gordona sp. CYKS1 was measured, using DBT dissolved in hexadecane as a sole sulfur source: 1 ml of DBT in 10 mM hexadecane was added to 20 ml of sterilized minimal salt medium containing 10 g/l of glucose. After inoculation of Gordona sp. CYKS1 at 33, changes in DBT concentration were observed analogously as in Example 2. As shown in FIG. 2, the concentration decreased from 10 mM to 0.34 mM after 60 hours of incubation, which indicates the elimination of DBT from the medium in an efficient and speedy manner.

EXAMPLE 4

Desulfurizing Activity of Gordona sp. CYKS1 for Various Organic Sulfur Compounds Desulfurizing activities of Gordona sp. CYKS1 for various organic sulfur compounds which have been known to be contained in petroleum were measured. As shown in Table 2, desulfurizing activities were valid for other thiophene derivatives, sulfides, disulfides and thiazole derivatives. In Table 2, the absorbance at 600 nm represents the concentration of cell culture after 4 days incubation using each of the said sulfur compounds as a sole sulfur source.

TABLE 2

Utilization of various organic compounds of Gordona sp. CYKS1 (KCTC 0431BP)

| Organic Sulfur Compounds | Absorbance (at 600 nm) |
| --- | --- |
| Methyl sulfide | 2.04 |
| Thiophene | 2.14 |
| Thiazole | 2.20 |
| 2-methyl thiophene | 2.22 |
| 3-methyl thiophene | 2.20 |
| 4,5-dimethyl thiazole | 1.86 |
| Thianaphthene | 1.86 |
| Trithiane | 0.08 |
| Phenyl sulfide | 1.89 |
| Dibenzothiophene | 1.93 |

TABLE 2-continued

Utilization of various organic compounds of Gordona sp. CYKS1 (KCTC 0431BP)

| Organic Sulfur Compounds | Absorbance (at 600 nm) |
| --- | --- |
| 2-methyl-β-naphthiothiazole | 2.28 |
| Benzyl sulfide | 1.82 |
| Thianthrene | 0.05 |
| p-tolyl disulfide | 1.89 |
| Benzyl disulfide | 2.20 |
| Dibenzothiophene sulfone | 2.30 |
| Benzyl sulfone | 0.06 |
| 4,4-thiodiphenol | 0.02 |

EXAMPLE 5

Desulfurizing Activity of Gordona sp. CYKS1 for Diesel Oil

To measure desulfurizing activity for diesel oil, 1 ml of light gas oil ("LGO") containing 0.3 wt % of sulfur was mixed with 20 ml of glucose-minimal salt medium in an analogous manner as in Example 2. For 72 hours after inoculation, changes of sulfur content in diesel oil were monitored by gas chromatography through HP-5 column (30 cm×0.5 mm×0.32 μm) and SCD (sulfur chemiluminescence detector) for selective detection of sulfur compounds. The condition for GC (gas chromatography) analysis was as followings: The temperature of inlet was maintained at 250° C., and the temperature of oven was controlled at 120° C. for initial 2 minutes and elevated up to 300° C. gradually at a rate of 10° C./min then held at 300° C. for 2 minutes. Nitrogen gas flowed into column at a rate of 2.0 ml/min. SCD was maintained at a temperature of 770–780 C., and the flow rates of hydrogen gas and air were 100 ml/min and 40 ml/min, respectively.

Figure 3:
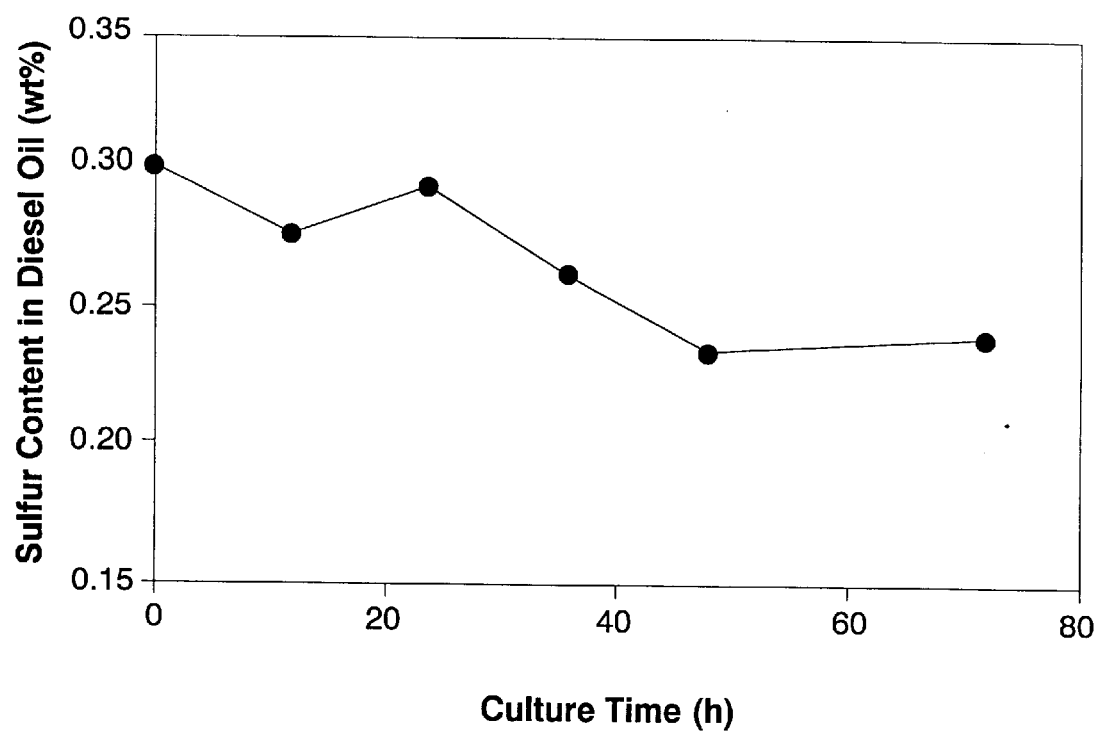
FIG. 3 is a graph showing the changes in sulfur content in diesel oil treated with Gordona sp. CYKS1.
Figure 4:
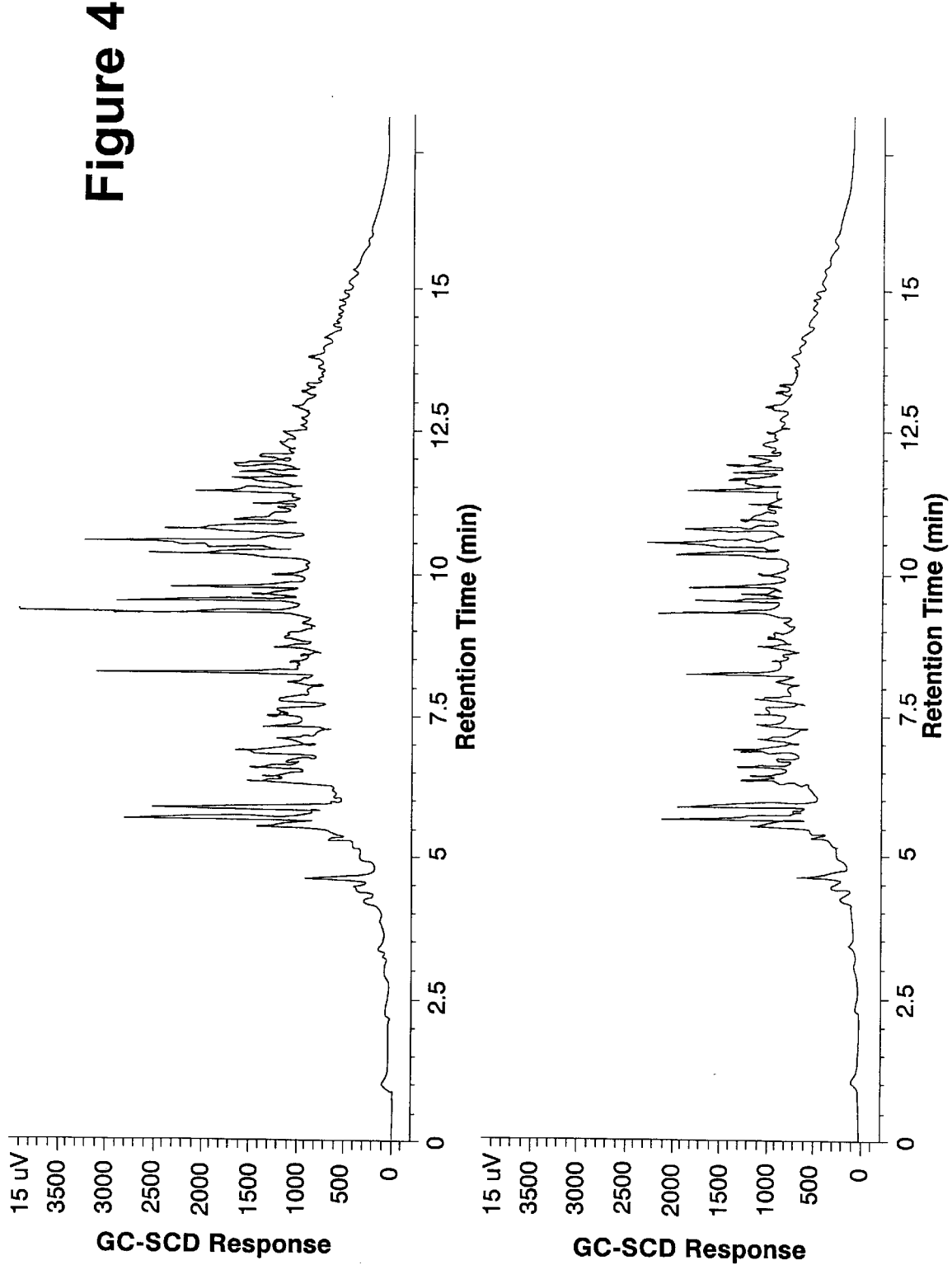
FIG. 4 is a GC-SCD chromatogram of diesel oil treated with Gordona sp. CYKS1 for 48 hours.

As shown in FIG. 3, after 48 hours of incubation, sulfur content in diesel oil decreased from 0.3 wt % to 0.235 wt %. GC-SCD chromatogram of diesel oil indicated that various organic sulfur compounds, which have more complex structure than that of DBT, can be readily desulfurized rather than DBT (see: FIG. 4). In FIG. 4, the upper and lower chromatograms show the signals before and after desulfurization by Gordona sp. CYKS1. Since the conventional chemical methods only allows the desulfurization of organic sulfur compounds, having more simple structure and shorter retention time in GC-SCD than DBT, the biological method can be applied for the desulfurization of various of organic sulfur compounds to make up for the technical limitation of chemical methods.

EXAMPLE 6

Desulfurizing Activity of Gordona sp. CYKS1 as Whole Cell Enzyme

Gordona sp. CYKS1 cultured with DBT as a sole sulfur source, was harvested by centrifugation and washed twice with isotonic solution (NaCl, 0.85%), resuspended in 0.1M phosphate buffer, and LGO was added to the slurry at the volume ratio 1:10 (organic phase:aqueous phase). After 12 hours, reduction of sulfur content was observed from 0.3 wt % to 0.24 wt % as shown in FIG. 5. In FIG. 5, the upper and lower chromatogram depicts the signals before and after desulfurization.

As clearly demonstrated and explained above, the present invention provides a novel Gordona sp. CYKS1 capable of selective removal of organically bound sulfurs from carbonaceous fossil fuel such as petroleum and coal by cleaving bonds between carbon and sulfur atoms of the said sulfur-containing organic compounds, and a method for biological desulfurization using this strain at the room temperature and atmospheric pressure. The method for biological desulfurization employing Gordona sp. CYKS1 has advantages over the conventional chemical methods as followings: The desulfurization can be carried out at a mild condition; the cost for installation and operation of equipments can be reduced; and, the desulfurization of highly complex organic sulfur compounds can be realized.

What is claimed is:
1. A biologically pure culture of Gordona sp. CYKS1 (KCTC 0431BP) capable of utilizing organic sulfur material as a sole sulfur source.

* * * * *